(12) United States Patent
Nageri et al.

(10) Patent No.: US 9,987,482 B2
(45) Date of Patent: Jun. 5, 2018

(54) SYSTEMS AND METHODS FOR MAKING AND USING REVERSIBLE MECHANICAL LEAD ANCHORS FOR ELECTRICAL STIMULATION SYSTEMS

(71) Applicant: Boston Scientific Neuromodulation Corporation, Valencia, CA (US)

(72) Inventors: Ranjan Krishna Mukhari Nageri, Valencia, CA (US); Geoffrey Abellana Villarta, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 271 days.

(21) Appl. No.: 14/720,708

(22) Filed: May 22, 2015

(65) Prior Publication Data

US 2015/0343198 A1    Dec. 3, 2015

Related U.S. Application Data

(60) Provisional application No. 62/003,502, filed on May 27, 2014.

(51) Int. Cl.
  *A61N 1/05*    (2006.01)
  *A61N 1/36*    (2006.01)

(52) U.S. Cl.
  CPC .... *A61N 1/0558* (2013.01); *A61N 2001/0582* (2013.01)

(58) Field of Classification Search
  CPC ................ A61N 1/0558; A61N 2001/0582
  See application file for complete search history.

(56) References Cited

U.S. PATENT DOCUMENTS

| 3,866,615 A | 2/1975 | Hewson |
| 4,141,752 A | 2/1979 | Shipko |
| 4,276,882 A | 7/1981 | Dickhudt et al. |
| 4,316,471 A | 2/1982 | Shipko et al. |
| 4,462,401 A | 7/1984 | Burgio |
| 4,632,679 A | 12/1986 | Mueller, Jr. |

(Continued)

FOREIGN PATENT DOCUMENTS

| EP | 85417 A1 | 8/1983 |
| EP | 0597213 A1 | 5/1994 |

(Continued)

*Primary Examiner* — Mark W Bockelman
(74) *Attorney, Agent, or Firm* — Lowe Graham Jones PLLC; Bruce E. Black (57) ABSTRACT

A lead anchor includes a flexible housing having a first end and a second end opposite to the first end, the flexible housing defining a lead lumen forming a continuous passageway through the flexible housing. The lead anchor also includes a compressible retention ring disposed within the flexible housing and around a portion of the lead lumen. The retention ring defines an uncompressed position in which the retention ring has an elongate shape, with a major axis and a minor axis, to hold a portion of a lead received within the lead lumen. The retention ring further defines a compressed position achieved by compressing opposite ends of the major axis of the retention ring to transition the retention ring to a more circular shape that allows the lead to slidingly pass through the retention ring. Upon release of the compression, the retention ring returns to the uncompressed position.

20 Claims, 9 Drawing Sheets

(56) References Cited

U.S. PATENT DOCUMENTS

| | | |
|---|---|---|
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,158,097 A | 10/1992 | Christlieb |
| 5,228,248 A | 7/1993 | Haddock |
| 5,376,108 A | 12/1994 | Collins et al. |
| 5,484,445 A | 1/1996 | Knuth |
| 5,865,843 A | 2/1999 | Baudino |
| 5,957,968 A | 9/1999 | Belden et al. |
| 6,181,969 B1 | 1/2001 | Gord |
| 6,192,279 B1 | 2/2001 | Barreras, Sr. et al. |
| 6,360,750 B1 | 3/2002 | Gerber et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,894,145 B2 | 5/2005 | Xiao et al. |
| 6,901,287 B2 | 5/2005 | Davis et al. |
| 6,978,180 B2 | 12/2005 | Tadlock |
| 7,069,083 B2 | 6/2006 | Finch et al. |
| 7,072,719 B2 | 7/2006 | Vinup et al. |
| 7,161,461 B1 | 1/2007 | Nelson |
| 7,244,150 B1 | 7/2007 | Brase et al. |
| 7,343,202 B2 | 3/2008 | Mrva et al. |
| 7,437,193 B2 | 10/2008 | Parramon et al. |
| 7,447,546 B2 | 11/2008 | Kim et al. |
| 7,610,102 B2 | 10/2009 | Kowalczyk |
| 7,672,734 B2 | 3/2010 | Anderson et al. |
| 7,761,165 B1 | 7/2010 | He et al. |
| 7,787,960 B2 | 8/2010 | Lubenow |
| 7,848,803 B1 | 12/2010 | Jaax et al. |
| 7,853,321 B2 | 12/2010 | Jaax et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,249,720 B2 * | 8/2012 | Verzal .................. A61N 1/057 606/232 |
| 8,315,704 B2 | 11/2012 | Jaax et al. |
| 8,364,278 B2 | 1/2013 | Pianca et al. |
| 8,706,229 B2 * | 4/2014 | Lahti .................. A61N 1/3752 607/37 |
| 9,038,258 B2 * | 5/2015 | Liao .................. F16L 19/06 29/447 |
| 2001/0000187 A1 | 4/2001 | Peckham et al. |
| 2002/0107554 A1 | 8/2002 | Biggs et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0206162 A1 | 9/2006 | Wahlstrand et al. |
| 2007/0050005 A1 | 3/2007 | Lauro |
| 2007/0078399 A1 | 4/2007 | Olson |
| 2007/0150036 A1 | 6/2007 | Anderson |
| 2007/0219595 A1 | 9/2007 | He |
| 2007/0255369 A1 | 11/2007 | Bonde et al. |
| 2008/0071320 A1 | 3/2008 | Brase |
| 2008/0091255 A1 | 4/2008 | Caparso et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0228251 A1 | 9/2008 | Hill |
| 2008/0243220 A1 | 10/2008 | Barker |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0198312 A1 | 8/2009 | Barker |
| 2009/0254151 A1 | 10/2009 | Anderson et al. |
| 2009/0270940 A1 | 10/2009 | Deininger et al. |
| 2010/0174240 A1 | 7/2010 | Wells et al. |
| 2010/0274336 A1 | 10/2010 | Nguyen-Stella et al. |
| 2010/0312319 A1 | 12/2010 | Barker |
| 2011/0022142 A1 | 1/2011 | Barker et al. |
| 2011/0060395 A1 | 3/2011 | Cantlon |
| 2011/0178573 A1 | 7/2011 | Nguyen-Stella et al. |
| 2012/0150202 A1 | 6/2012 | Chen et al. |
| 2012/0185027 A1 | 7/2012 | Pianca et al. |
| 2012/0232626 A1 | 9/2012 | Daglow |
| 2012/0277670 A1 | 11/2012 | Goetz |
| 2012/0330355 A1 | 12/2012 | Finley et al. |
| 2013/0204336 A1 | 8/2013 | Sharma |
| 2014/0148851 A1 * | 5/2014 | Finley ................. A61B 17/0401 606/232 |
| 2015/0005856 A1 | 1/2015 | Pianca et al. |
| 2015/0005859 A1 * | 1/2015 | Thacker ............... A61N 1/0558 607/117 |
| 2015/0045865 A1 | 2/2015 | Nageri et al. |
| 2015/0051674 A1 | 2/2015 | Barner et al. |
| 2015/0051675 A1 | 2/2015 | Barner |

FOREIGN PATENT DOCUMENTS

| | | |
|---|---|---|
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2013112920 A1 | 8/2013 |

* cited by examiner

SYSTEMS AND METHODS FOR MAKING AND USING REVERSIBLE MECHANICAL LEAD ANCHORS FOR ELECTRICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/003,502, filed May 27, 2014, which is incorporated herein by reference.

FIELD

The present invention is directed to the area of implantable electrical stimulation systems and methods of making and using the systems. The present invention is also directed to implantable electrical stimulation systems that include lead anchors for anchoring leads to patient tissue, as well as methods of making and using the leads, lead anchors, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead anchor includes a flexible housing having a first end and a second end opposite to the first end, the flexible housing defining a lead lumen forming a continuous passageway through the flexible housing, the lead lumen having a first opening defined along the first end of the flexible housing and a second opening defined along the second end of the flexible housing. The lead anchor also includes a compressible retention ring disposed within the flexible housing and around a portion of the lead lumen. The retention ring defines an uncompressed position in which the retention ring has an elongate shape, with a major axis and a minor axis, to hold a portion of a lead, if present, received within the lead lumen. The retention ring further defines a compressed position achieved by compressing opposite ends of the major axis of the retention ring to transition the retention ring to a more circular shape that allows the lead to slidingly pass through the retention ring. Upon release of the compression, the retention ring returns to the uncompressed position.

In at least some embodiments, the retention ring is formed from a metal material. In at least some embodiments, in the uncompressed position, the retention ring has an oval shape. In at least some embodiments, the retention ring has an interior surface and the interior surface has surface features which facilitate holding the portion of the lead. In at least some embodiments, the surface features are selected from serrations, sharp teeth, or non-sharp teeth. In at least some embodiments, the first end of the flexible housing has an elongated, tapered shape.

In at least some embodiments, the lead anchor also includes two tabs extending from the flexible housing on opposite sides of the flexible housing with an eyelet formed in each tab. In at least some embodiments, the major axis of the retention ring is in a plane parallel to a plane defined by the two tabs. In at least some embodiments, the major axis of the retention ring is in a plane perpendicular to a plane defined by the two tabs. In at least some embodiments, the two tabs are longitudinally offset. In at least some embodiments, at least a portion of the retention ring is disposed between the two tabs. In at least some embodiments, the two tabs are disposed at a same longitudinal position along the lead anchor. In at least some embodiments, the retention ring is disposed between the two tabs.

Another embodiment is an implantable stimulation arrangement that includes the lead anchor described above and an electrical stimulation lead having an electrode array. The lead anchor is configured and arranged for receiving a portion of the electrical stimulation lead and removably retaining the received portion of the electrical stimulation lead.

A further embodiment is an implantable stimulation device that includes the lead anchor describe above; an electrical stimulation lead having an electrode array and coupleable to the lead anchor; and a control module coupleable to the electrical stimulation lead.

Yet another embodiment is a method of implanting an implantable stimulation device. The method includes providing the lead anchor describe above; advancing an electrode array of an electrical stimulation lead into a patient to a target stimulation location; compressing the retention ring of the lead anchor to the compressed position and sliding the lead anchor along the electrical stimulation lead to a desired placement position along the electrical stimulation lead with a portion of the electrical stimulation lead disposed within the lead lumen of the lead anchor; and releasing the compression of the retention ring so that the retention ring returns to the uncompressed position and holds the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems that include lead anchors for anchoring leads to patient tissue, as well as methods of making and using the leads, lead anchors, and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
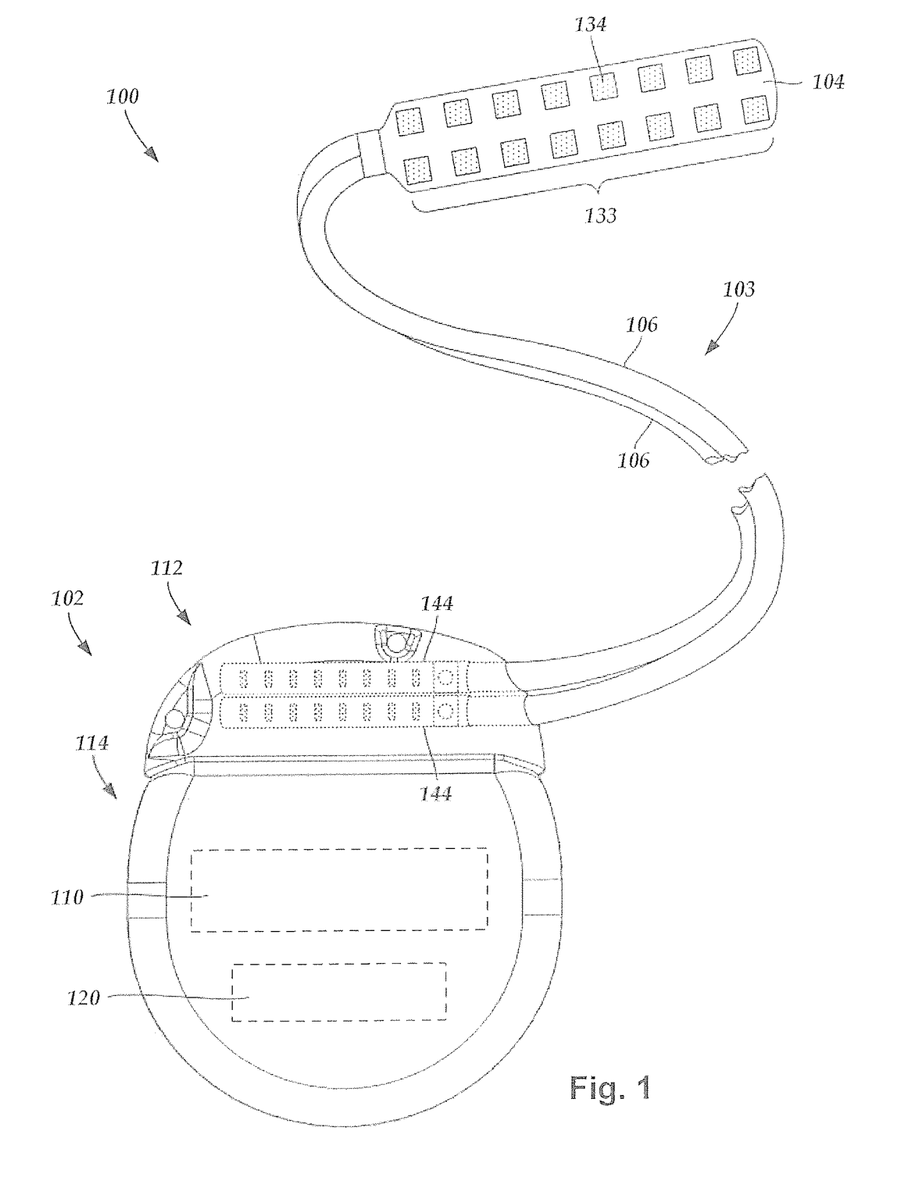
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
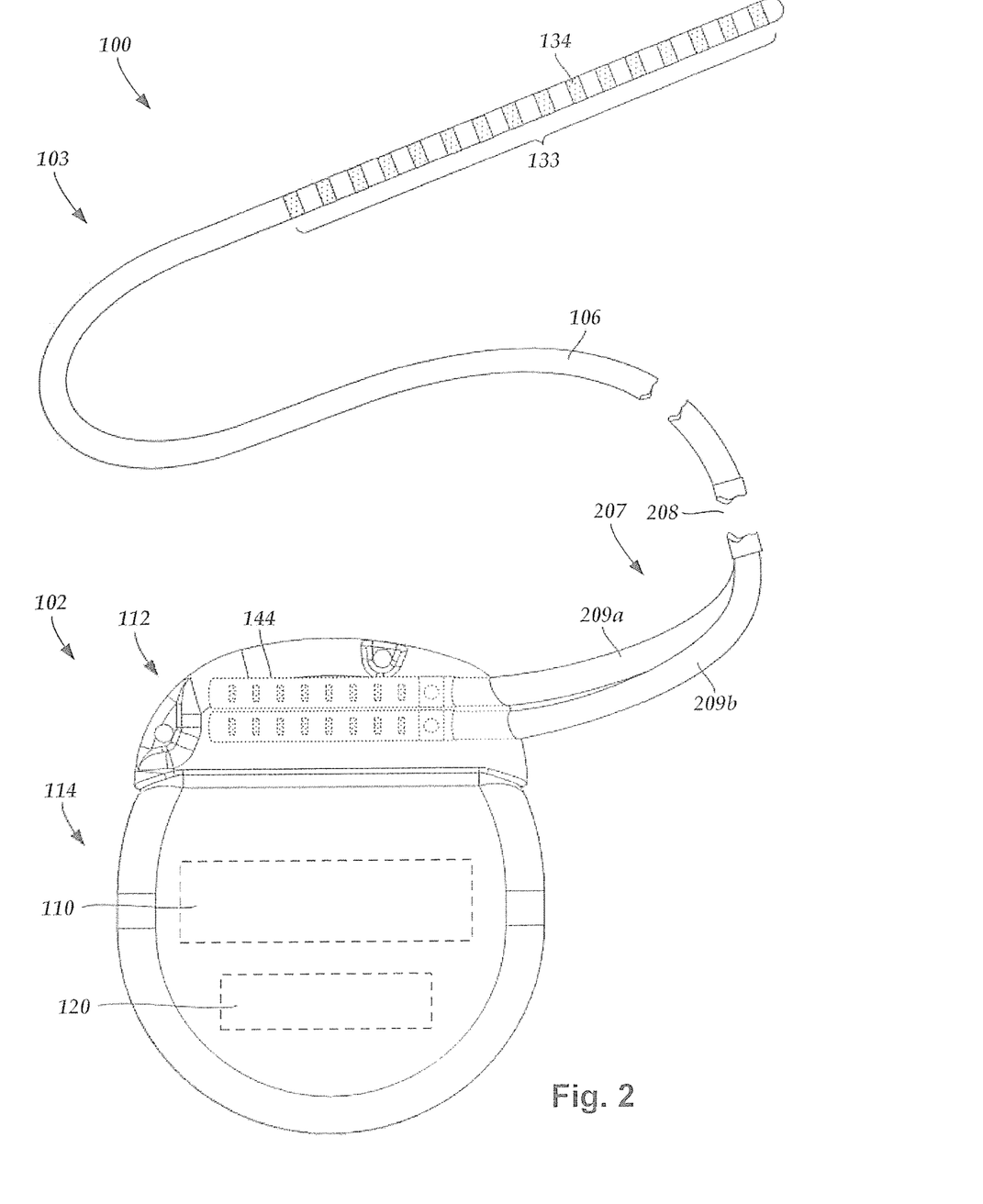
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some embodiments, the lead 103 includes a single proximal end portion. In at least some other embodiments, the lead 103 includes two or more proximal end portions ("tails").

Figure 3A:
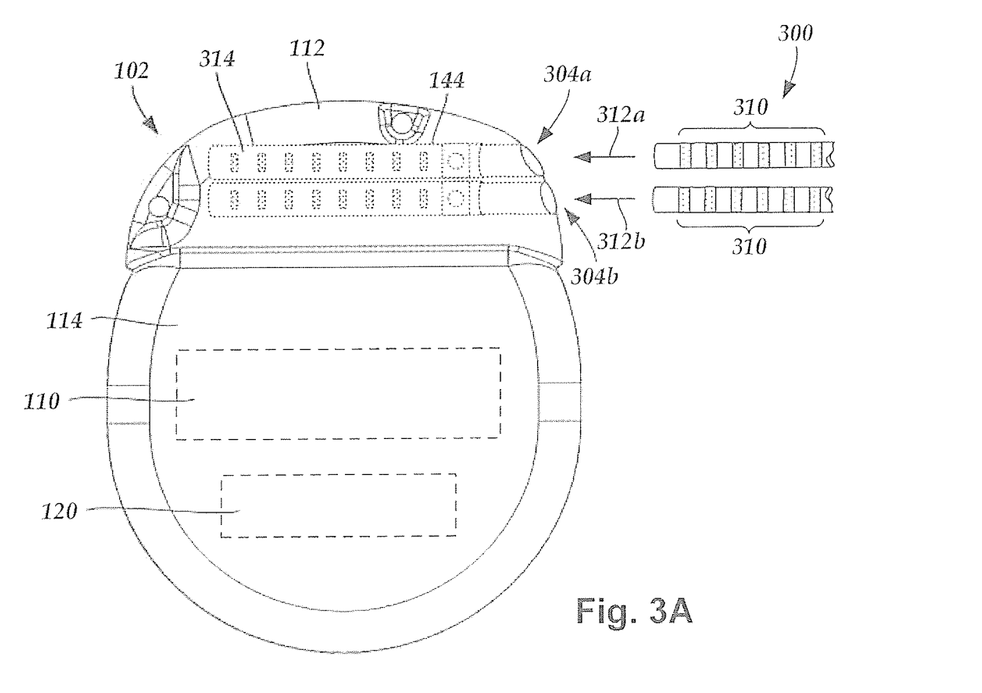
FIG. 3A is a schematic view of one embodiment of the control module of FIG. 1 configured and arranged to electrically couple to an elongated device, according to the invention.
Figure 3B:
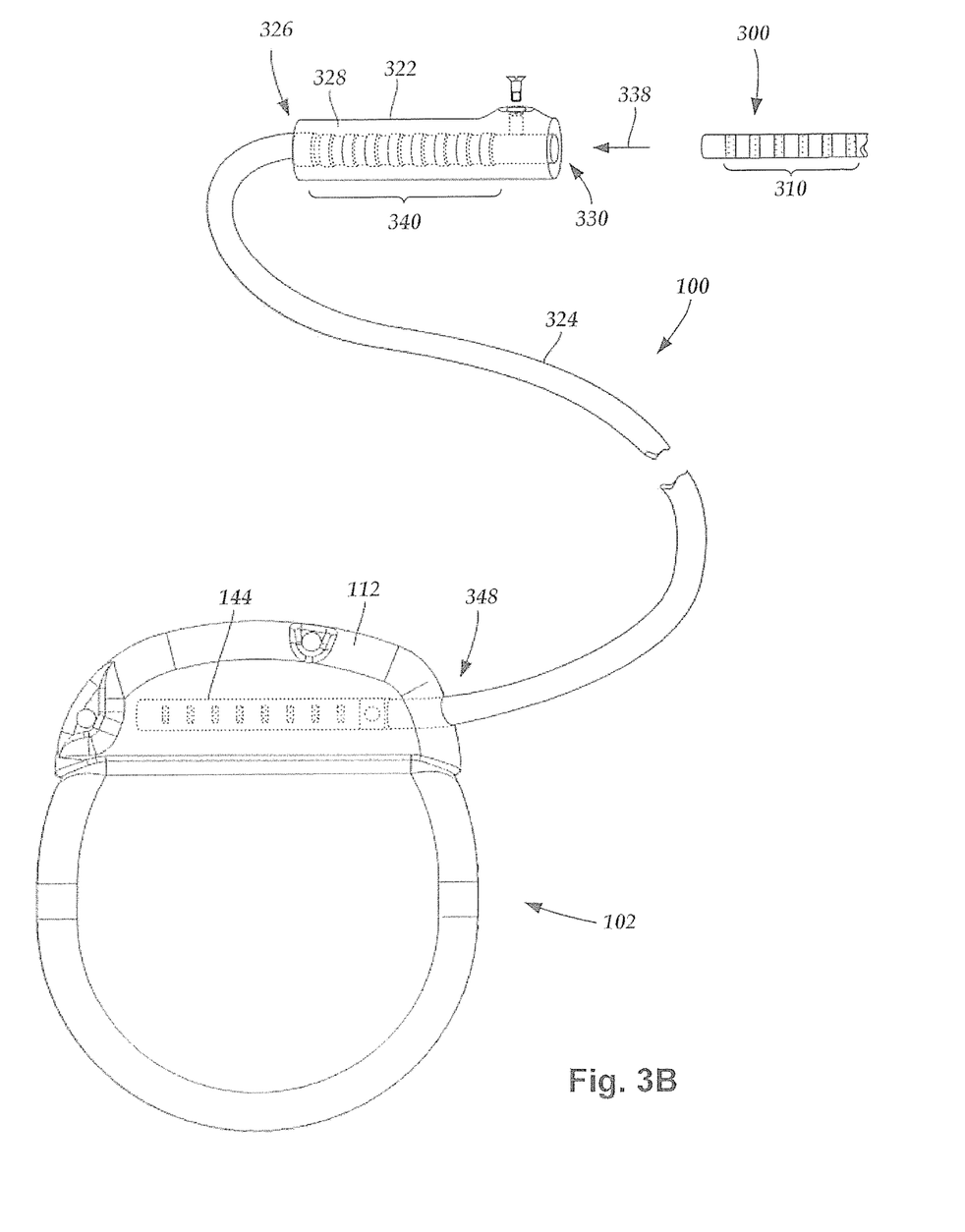
FIG. 3B is a schematic view of one embodiment of a lead extension configured and arranged to electrically couple the elongated device of FIG. 2 to the control module of FIG. 1, according to the invention.

In at least some embodiments, the lead 103 couples to the control module 102 via one or more intermediate devices (300 in FIGS. 3A-3B). For example, in at least some embodiments one or more lead extensions 324 (see e.g., FIG. 3B) are disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector inner housing 112 and a sealed electronics inner housing 114. An electronic subassembly 110 and an optional power source 120 are disposed in the electronics inner housing 114. A control module connector 144 is disposed in the connector inner housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector inner housing 112 is shown having two ports 304a and 304b. The connector inner housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector inner housing 328. The connector inner housing 328 defines at least one port 330 into which terminals 310 of the elongated device 300 can be inserted, as shown by directional arrow 338. The connector inner housing 328 also includes a plurality of connector contacts, such as connector contact 340. When the elongated device 300 is inserted into the port 330, the connector contacts 240 disposed in the connector inner housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 are electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead anchor can be used in an implantable device, such as an implantable spinal cord stimulator or any other stimulator system, to anchor a lead or lead extension to patient tissue. The lead anchor will be described herein as anchoring a lead, but it will be understood that the lead anchor can also anchor a lead extension within the patient's body.

Figure 4A:
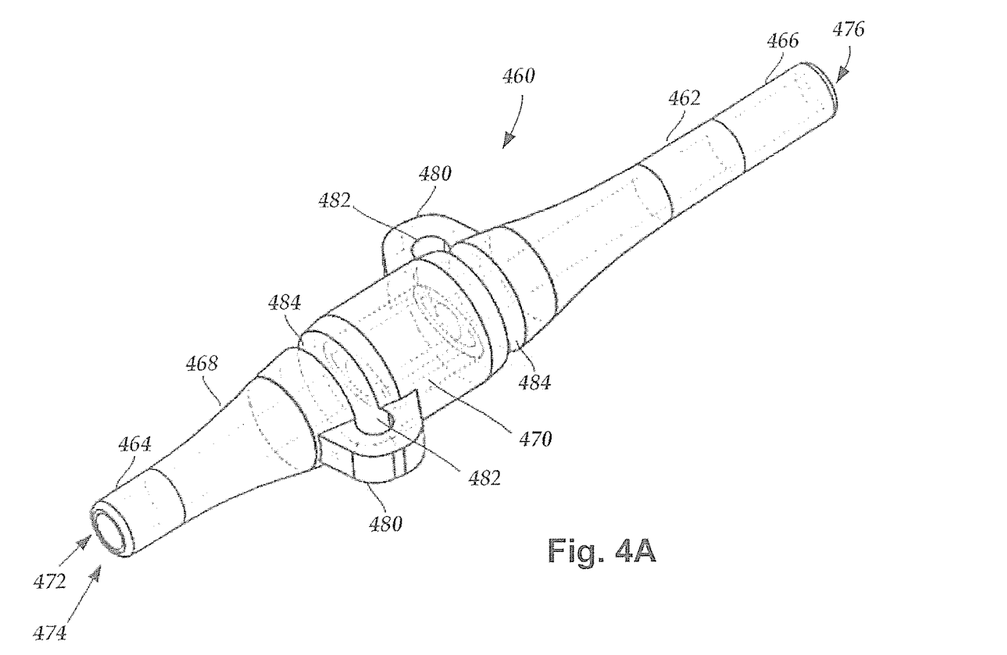
FIG. 4A is a schematic perspective view of one embodiment of a lead anchor, according to the invention.
Figure 4B:
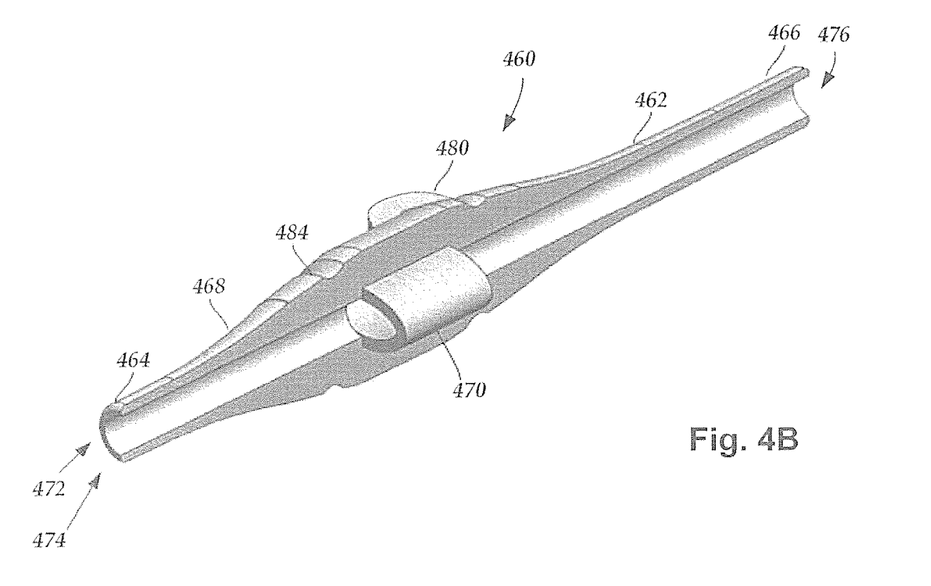
FIG. 4B is a schematic perspective view of the lead anchor of FIG. 4A with half of the flexible housing removed, according to the invention.

The lead anchor includes a compressible retention ring to retain a portion of the lead body within the lead anchor. FIGS. 4A-4B illustrate one embodiment of a lead anchor 460 which includes a flexible housing 462 and a compressible retention ring 470 disposed within the flexible housing. FIG. 4B illustrates the lead anchor 470 with half of the flexible housing 462 removed to illustrate interior features of the lead anchor.

The flexible housing 462 has a first end 464, a second end 466 opposite to the first end, and an outer surface 468. The flexible housing 462 includes a lead lumen 472, which provides a continuous passageway through the flexible housing 462 between the first end 464 and the second end 466. The lead lumen 472 includes a first opening 474 defined along the first end 464 and a second opening 476 defined along the second end 466. The lead lumen 472 is dimensioned to receive a portion of a lead, such as the lead 103, from either of the first opening 474 or the second opening 476. The lead lumen 472 receives the lead such that the lead typically extends from both the first opening 474 and the second opening 476 when the lead is anchored with the lead anchor 460.

The flexible housing 462 can be formed using any suitable biocompatible material such as, but not limited to, polyvinyl chloride, polyurethane, silicone, thermoplastic polyesters, polycarbonate fluoropolymers, and the like.

In at least some embodiments, one or more of the ends 464, 466 of the flexible housing 462 are elongated, as illustrated in FIGS. 4A-4B. In at least some embodiments, one or more of the ends 464, 466 are tapered, as illustrated in FIGS. 4A-4B. The length and tapering of the ends 464, 466 can be the same or can be different for the two ends, as illustrated in FIGS. 4A-4B. The flexible housing 462 may have any suitable shape including, for example, oblong, rectangular, cylindrical, elliptical, or the like, or any other regular or irregular shape, or the like. In some embodiments, the flexible housing 462 has a variable diameter that increases from one end to a middle or an interior portion, and then decreases from the interior portion to the opposite end, as illustrated in FIGS. 4A-4B. Alternatively, the flexible housing 462 may define a uniform diameter along all or a portion of its length.

The flexible housing 462 can include one or more optional tabs 480 with eyelets 482 for receiving a suture, a staple, or the like, for securing the lead anchor 460 to patient tissue. The tabs 480 may be circumferentially and axially disposed at any suitable location around the flexible housing 462. In at least some embodiments, the tabs 480 with eyelets 482 are circumferentially offset by 180° from one another (or disposed on opposite sides of the flexible housing 462) as illustrated in FIG. 4A. In at least some embodiments, the tabs 480 are also axially or longitudinally offset from each other as illustrated in FIG. 4A. The compressible retention ring 470 may be disposed between (inclusively or exclusively of) the axial positions of the two tabs 480, as illustrated in FIG. 4B. The lead anchor 460 can include any suitable number of tabs 480 including, for example, one, two, three, four, five, six, seven, eight, or more tabs 480. The tabs 480 may be made from either the same material or different material from the flexible housing 462.

In at least some embodiments, the flexible housing 462 includes one or more optional suture channels 484 that are disposed at least partially around a circumference of the flexible housing 462. In at least some embodiments, a suture channel 484 is also axially-aligned with one or more of the tabs 480 and eyelets 482, as illustrated in FIG. 4A. The suture channels 484 facilitate suturing of the lead anchor 460 to patient tissue by enabling sutures to be disposed around the flexible housing 462 and passed through one or more of the eyelets 482 without increasing the diameter of the lead anchor 460, while also preventing (or reducing the likelihood of) the sutures from slipping off of an end of the flexible housing 462.

Figure 7A:
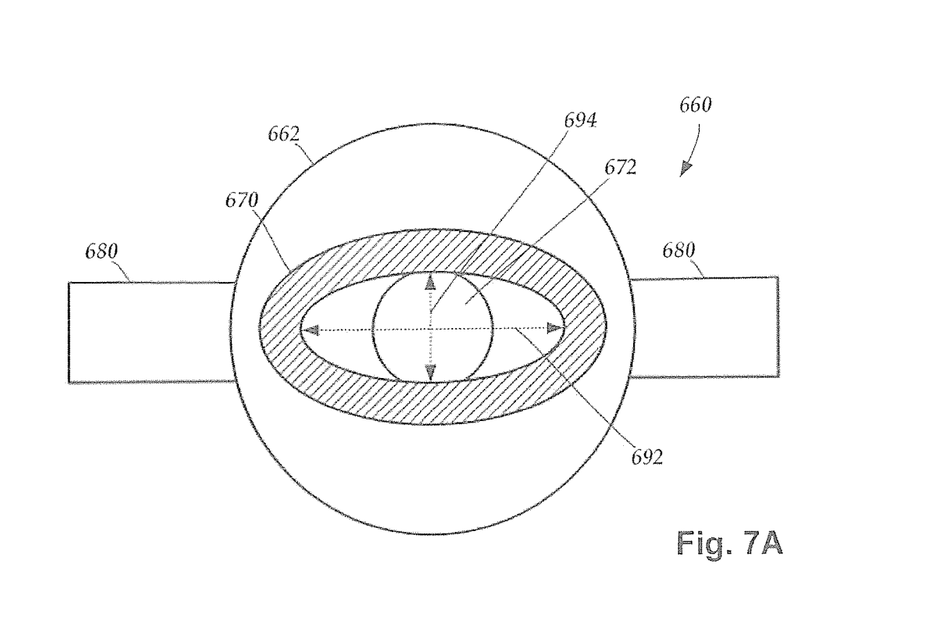
FIG. 7A is a schematic cross-sectional view of one embodiment of the lead anchor of FIG. 6 in an uncompressed position, according to the invention.
Figure 7B:
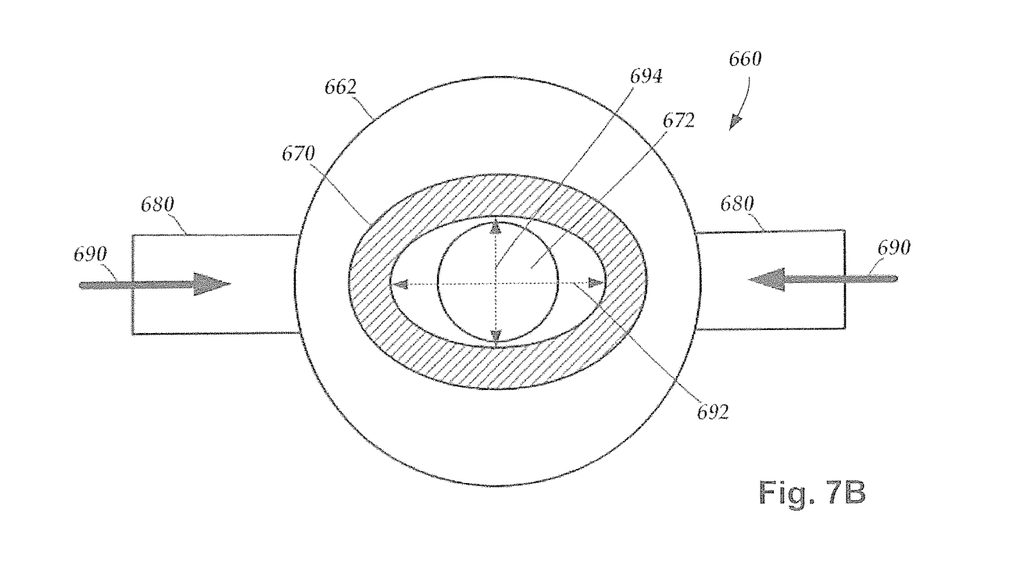
FIG. 7B is a schematic cross-sectional view of the lead anchor of FIG. 7A in a compressed position, according to the invention.
Figure 8A:
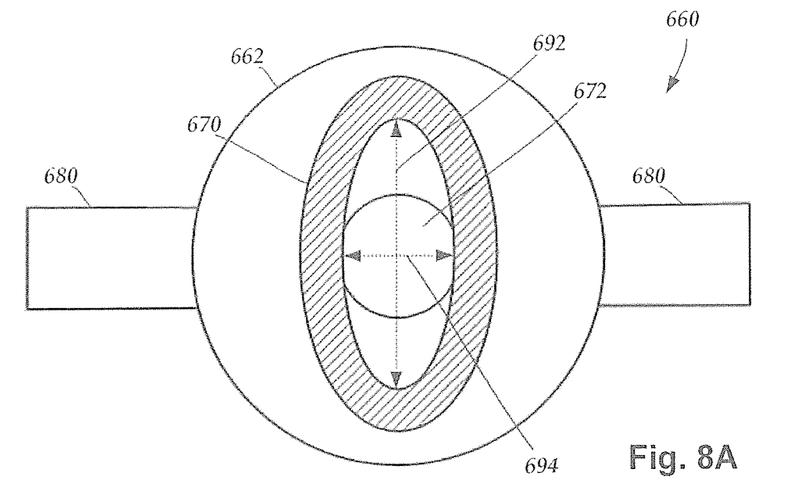
FIG. 8A is a schematic cross-sectional view of another embodiment of the lead anchor of FIG. 6 in an uncompressed position, according to the invention.

The compressible retention ring 470 has a non-circular cross-sectional shape when in the uncompressed position (see, for example, retention ring 670 in FIGS. 7A and 8A). The retention ring 470 can be compressed by the fingers of a user, or by using a tool, such as a clamp or forceps or the like, operated by the user, to achieve a compressed position (see, for example, retention ring 670 in FIGS. 7B and 8B). The retention ring 470, in the uncompressed position, grips or otherwise holds the portion of the lead that passes through the portion of the lead lumen 472 encompassed by the retention ring 470 and anchors the lead to the lead anchor 460. In the compressed position, the retention ring 470 allows the lead to slide through the retention ring 470 and the lead anchor 460 can be placed at the desired position along the lead. In at least some embodiments, the retention ring 470 forms a more circular shape in the compressed position than the retention ring has in the uncompressed position (compare, FIG. 7A with FIG. 7B and FIG. 8A with FIG. 8B.) Preferably, when not compressed, the retention ring 470 is configured to return to the uncompressed position. In at least some embodiments, the uncompressed position is the preferential position of the retention ring 470.

The retention ring 470 can be made of any suitable material that is sufficiently rigid to grip or otherwise hold the lead when in the uncompressed position, but can also be deformed or flexed when compressed, as described below, to assume the compressed position. Examples of suitable materials include, but are not limited to, spring (e.g., heat tempered) steel, stainless steel; other metals, alloys, and polymers; or the like. In at least some embodiments, the material of the retention ring 470 is selected to have sufficient longevity or endurance so that the retention ring can be compressed and uncompressed several times allowing the lead anchor 460 to be repositioned along the lead.

The retention ring 470 can have any suitable dimensions as long as it fits within the flexible housing 462 and can be compressed to allow the lead to slide through the ring. In some embodiments, the retention ring 470 has a longitudinal length (along the axis defined by the lead lumen 472) of at least 2 mm, at least 5 mm, or at least 1 cm, or up to 2 cm.

In the illustrated embodiment of FIGS. 4A and 4B, a major axis of the retention ring 470 in the uncompressed position is in a plane parallel to a plane defined by the tabs 480, as describe below. In at least some embodiments, the retention ring 470 (or a portion of the retention ring) is disposed longitudinally between the tabs 480 so that the user has a visual indication of where to compress the lead anchor 460 to compress the retention ring.

Figure 5:
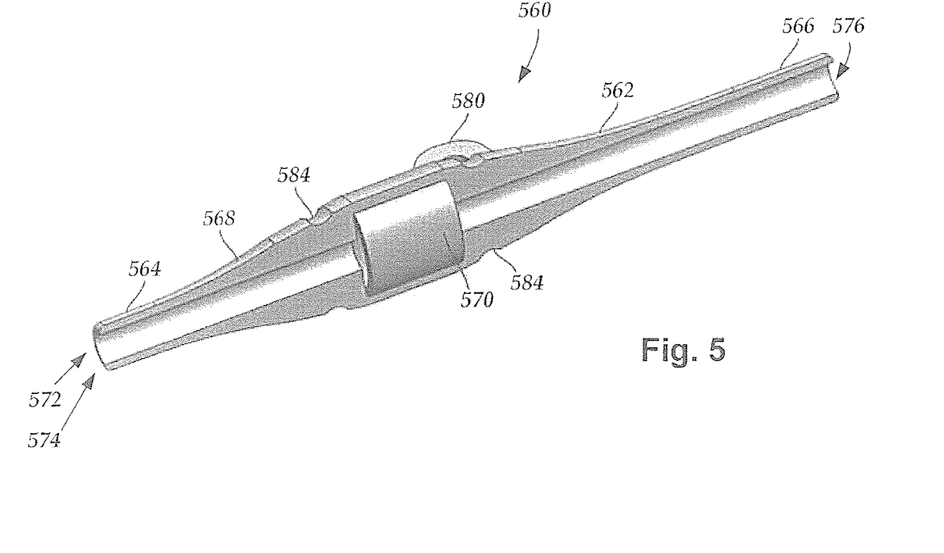
FIG. 5 is a schematic perspective view of a second embodiment of a lead anchor with half of the flexible housing removed, according to the invention.

FIG. 5 illustrates a second embodiment of a lead anchor 560 in which the major axis of the retention ring 570 in the uncompressed position is rotated by 90 degrees with respect to the embodiment of FIGS. 4A and 4B. In at least some embodiments, the major axis of the retention ring 570 is in a plane perpendicular to a plane defined by the tabs 580, as illustrated in FIG. 5. The lead anchor 560 includes a flexible housing 562 with a first end 564, second end 566, and outer surface 568, as well as a lead lumen 572 with a first opening 574 and second opening 576. The lead anchor also includes one or more optional tabs 580 with an eyelet (not shown) and one or more optional suture channels 584. The elements of lead anchor 560 are the same, and have the same design considerations and dimensions, as the similarly named elements of lead anchor 460, unless indicated otherwise.

Figure 6:
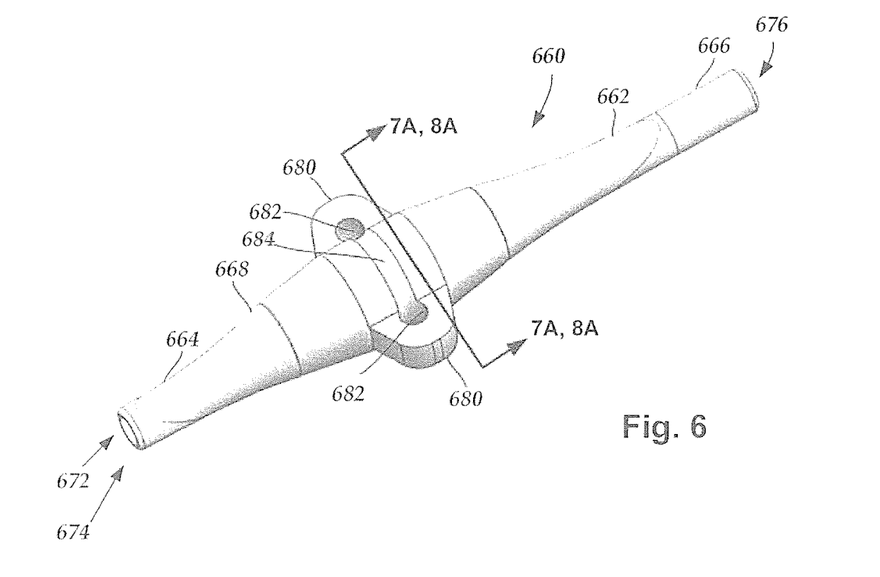
FIG. 6 is a schematic perspective view of a third embodiment of a lead anchor, according to the invention.

FIG. 6 illustrates a third embodiment of a lead anchor 660 that includes a compressible retention ring 670 (see, FIGS. 7A-8B) and a flexible housing 662 with a first end 664, second end 666, and outer surface 668, as well as a lead lumen 672 with a first opening 674 and second opening 676. The lead anchor also includes one or more optional tabs 680 with an eyelet 682 and one or more optional suture channels 684. The elements of lead anchor 660 are the same, and have the same design considerations and dimensions, as the similarly named elements of lead anchor 460, unless indicated otherwise.

In this embodiment, two suture tabs 680 are disposed opposite one another on the outer surface 668 of the flexible housing 662 in the same axial or longitudinal position. In some embodiments, the retention ring 670 (see, FIGS. 7A-8B) is disposed within the flexible housing 662 at a same longitudinal position as the tabs 680. This provides a visual indication to the user as to where the user should compress the lead anchor 660 to compress the retention ring 670.

FIGS. 7A and 7B illustrate, in cross-section, one embodiment of the lead anchor 660 with flexible housing 662, retention ring 670, lead lumen 672, and tabs 680 in the uncompressed position. It will be recognized that similar cross-sectional illustrations can be provided for lead anchor 460 with different placement of the tabs.

The retention ring 670 has a major (or long) axis 692 and a minor (or short) axis 694. The two axes 692, 694 define two axial inner diameters for the retention ring 670 which have different sizes in the uncompressed position, as illustrated in FIG. 7A. For example, a ratio of the diameter of the retention ring along the major axis to the diameter of the retention ring along the minor axis in the uncompressed position is at least 1.1:1, 1.2:1, 1.5:1, 2:1, or greater. In the illustrated embodiment, the retention ring has an oval shape, but other non-circular, elongate shapes can also be used that have major and minor axes with different axial inner diameters in the uncompressed position. In this embodiment, the major axis 692 is in a plane parallel to a plane defined by the two tabs 680. In the uncompressed position, the lead is gripped or otherwise held by the retention ring 672.

FIG. 7B illustrates the application of compression (or pressure), indicated by arrows 690, along the major axis 692 of the retention ring 670 to enter the compressed position. This causes the retention ring 670 to flex resulting in shortening of the inner axial diameter along the major axis and lengthening of the inner axial diameter along the minor axis. In some embodiments, the two axial diameters are equal in the compressed position. In other embodiments, the two axial inner diameters remain unequal in the compressed position. In the compressed position, the lead can slide along the lead lumen 672 and through the retention ring 672.

Figure 8B:
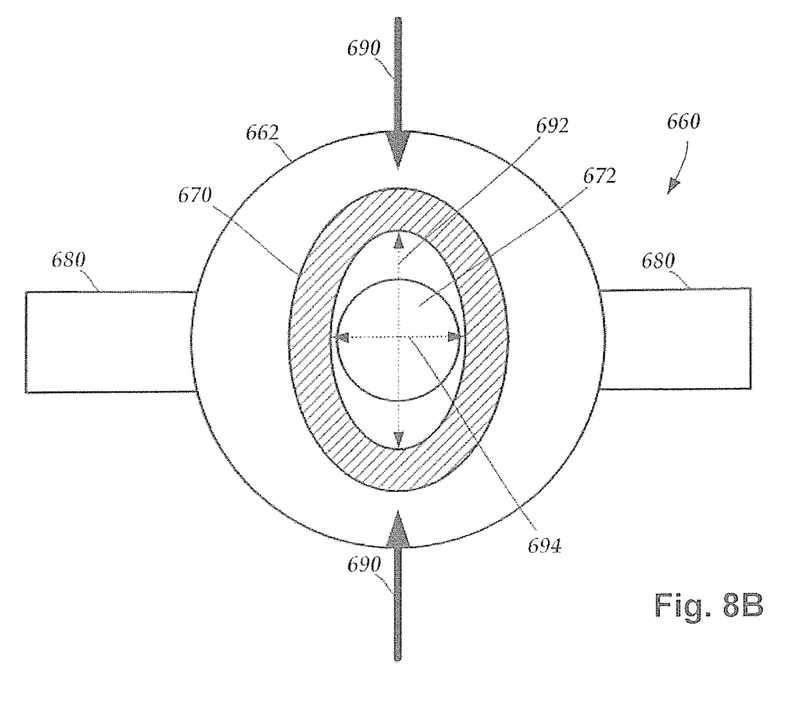
FIG. 8B is a schematic cross-sectional view of the lead anchor of FIG. 8A in a compressed position, according to the invention.

FIGS. 8A and 8B illustrate, in cross-section, a second embodiment of the lead anchor 660 with flexible housing 662, retention ring 670, lead lumen 672, and tabs 680 in the uncompressed position. It will be recognized that similar cross-sectional illustrations can be provided for lead anchor 560 with different placement of the tabs.

The retention ring 670 has a major (or long) axis 692 and a minor (or short) axis 694. The two axes 692, 694 define two axial inner diameters for the retention ring 670 which have different sizes in the uncompressed position, as illustrated in FIG. 8A. For example, a ratio of the diameter of the retention ring along the major axis to the diameter of the retention ring along the minor axis in the uncompressed position is at least 1.1:1, 1.2:1, 1.5:1, 2:1, or greater. In the illustrated embodiment, the retention ring has an oval shape, but other non-circular, elongate shapes can also be used that have major and minor axes which have different axial inner diameters in the uncompressed position. In this embodiment, the major axis 692 is in a plane perpendicular to a plane defined by the two tabs 680. In the uncompressed position, the lead is gripped or otherwise held by the retention ring 672.

FIG. 8B illustrates the application of compression (or pressure), indicated by arrows 690, along the major axis 692 of the retention ring 670 to enter the compressed position. This causes the retention ring 670 to flex resulting in shortening of the inner axial diameter along the major axis and lengthening of the inner axial diameter along the minor axis. In some embodiments, the two axial diameters are equal in the compressed position. In other embodiments, the two axial inner diameters remain unequal in the compressed position. In the compressed position, the lead can slide along the lead lumen 672 and through the retention ring 672.

FIGS. 7A and 8A illustrate two orientations of the retention ring 670 within the flexible housing 662 that are 90 degrees rotated with respect to each other. It will be recognized that any other angular orientation of the retention ring 670 within the flexible housing 662 can be utilized and can also be applied to retention rings 470, 570.

In at least some embodiments, any of the retention rings described above can include surface texture on the interior surface of the retention ring to facilitate gripping or otherwise holding the lead in the uncompressed position. Examples of surface texture include, but are not limited to, surface roughening, serrations, teeth (sharp or non-sharp), or the like.

In at least some embodiments, an electrode array of an electrical stimulation lead is advanced into a patient to a target stimulation location. The lead anchor is slid onto the lead with the retention ring compressed by the user using the user's fingers, a tool, or the like to assume a compressed position. When the desired placement of the lead anchor is achieved, the compression is removed so that the retention ring returns to the uncompressed position and grips or otherwise holds the lead. The lead anchor can be repositioned by again compressing the retention ring to allow the lead to slide through the lead anchor.

The lead anchor is anchored to patient tissue using, for example, suture or staples (or both) passed through eyelets formed along the lead anchor. The lead anchor may be disposed over, and attached to, a portion of the lead either before or after advancing the lead to the target stimulation location. The lead anchor may be anchored to patient tissue either before or after being disposed over, and attached to, a portion of the lead.

Figure 9:
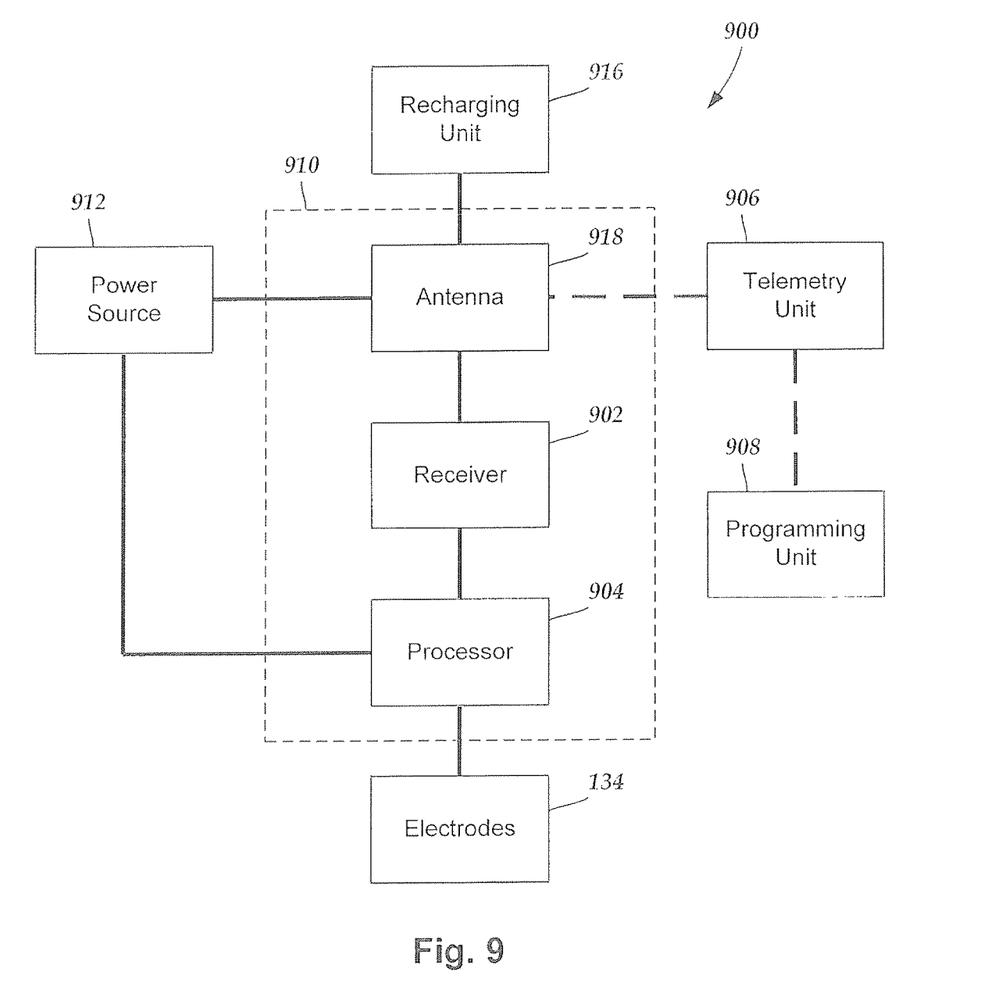
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed inner housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the scope of the invention, the invention also resides in the claims hereinafter appended.

What is claimed as new and desired to be protected by Letters Patent of the United States is:

1. A lead anchor comprising:
    a flexible housing having a first end and a second end opposite to the first end, the flexible housing defining a lead lumen forming a continuous passageway through the flexible housing, the lead lumen having a first opening defined along the first end of the flexible housing and a second opening defined along the second end of the flexible housing; and
    a compressible, metal retention ring disposed within the flexible housing and around a portion of the lead lumen, the retention ring defining an uncompressed position in which the retention ring has an elongate shape, with a major axis and a minor axis, that is configured and arranged to directly engage and hold a portion of a lead, if present, received within the lead lumen, the retention ring further defining a compressed position achieved by compressing opposite ends of the major axis of the retention ring to transition the retention ring to a more circular shape that allows the lead to slidingly pass through the retention ring, wherein, upon release of the compression, the retention ring is configured and arranged to return to the uncompressed position.

2. The lead anchor of claim 1, wherein the retention ring is made of spring steel or stainless steel.

3. The lead anchor of claim 1, further comprising two tabs extending from the flexible housing on opposite sides of the flexible housing with an eyelet formed in each tab.

4. The lead anchor of claim 3, wherein the major axis of the retention ring is in a plane parallel to a plane defined by the two tabs.

5. The lead anchor of claim 3, wherein the major axis of the retention ring is in a plane perpendicular to a plane defined by the two tabs.

6. The lead anchor of claim 3, wherein the two tabs are longitudinally offset.

7. The lead anchor of claim 6, wherein at least a portion of the retention ring is disposed between the two tabs.

8. The lead anchor of claim 3, wherein the two tabs are disposed at a same longitudinal position along the lead anchor.

9. The lead anchor of claim 8, wherein the retention ring is disposed between the two tabs.

10. The lead anchor of claim 1, wherein, in the uncompressed position, the retention ring has an oval shape.

11. The lead anchor of claim 1, wherein the retention ring has an interior surface and the interior surface has surface features which facilitate holding the portion of the lead.

12. The lead anchor of claim 11, wherein the surface features are selected from serrations, sharp teeth, or non-sharp teeth.

13. The lead anchor of claim 1, wherein the first end of the flexible housing has an elongated, tapered shape.

14. An implantable stimulation arrangement, comprising:
the lead anchor of claim 1; and
an electrical stimulation lead comprising an electrode array, wherein the lead anchor is configured and arranged for receiving a portion of the electrical stimulation lead and removably retaining the received portion of the electrical stimulation lead.

15. An implantable stimulation device, comprising:
the lead anchor of claim 1;
an electrical stimulation lead comprising an electrode array and coupleable to the lead anchor; and
a control module coupleable to the electrical stimulation lead.

16. A method of implanting an implantable stimulation device, the method comprising:
providing the lead anchor of claim 1;
advancing an electrode array of an electrical stimulation lead into a patient to a target stimulation location;
compressing the retention ring of the lead anchor to the compressed position and sliding the lead anchor along the electrical stimulation lead to a desired placement position along the electrical stimulation lead with a portion of the electrical stimulation lead disposed within the lead lumen of the lead anchor; and
releasing the compression of the retention ring so that the retention ring returns to the uncompressed position and holds the lead.

17. The method of claim 16, further comprising securing the lead anchor to patient tissue in proximity to the lead anchor.

18. The method of claim 16, further comprising coupling the electrical stimulation lead to a control module.

19. The method of claim 16, wherein the lead anchor comprises two tabs extending from the flexible housing on opposite sides of the flexible housing and at a same longitudinal position along the lead anchor,
wherein compressing the retention ring comprises compressing the lead anchor at the two tabs.

20. The method of claim 16, wherein the lead anchor comprises two tabs extending from the flexible housing on opposite sides of the flexible housing and longitudinally offset from each other,
wherein compressing the retention ring comprises compressing the lead anchor between the two tabs.

* * * * *